(12) United States Patent
Duncan et al.

(10) Patent No.: US 8,208,767 B2
(45) Date of Patent: Jun. 26, 2012

(54) SENSOR ARRAY CONFIGURATION FOR EXTENDING USEFUL SENSING LENGTH OF A SWEPT-WAVELENGTH INTERFEROMETRY BASED SYSTEM

(75) Inventors: Roger G. Duncan, Christiansburg, VA (US); Brooks A. Childers, Christiansburg, VA (US); Robert M. Harman, Troutville, VA (US)

(73) Assignee: Baker Hughes Incorporated, Houston, TX (US)

( * ) Notice: Subject to any disclaimer, the term of this patent is extended or adjusted under 35 U.S.C. 154(b) by 476 days.

(21) Appl. No.: 12/615,642

(22) Filed: Nov. 10, 2009

(65) Prior Publication Data

US 2011/0110621 A1    May 12, 2011

(51) Int. Cl.
*G02B 6/00* (2006.01)
*G02B 6/34* (2006.01)
*G02B 6/26* (2006.01)
*G01B 9/02* (2006.01)
*G01J 1/04* (2006.01)

(52) U.S. Cl. ........ 385/12; 385/37; 356/478; 250/227.18
(58) Field of Classification Search ............ 385/10, 385/12–14, 37, 147; 356/73.1, 478; 250/227.14, 250/227.18
See application file for complete search history.

(56) References Cited

U.S. PATENT DOCUMENTS

| 5,144,690 | A | * | 9/1992 | Domash ............ 385/12 |
| 5,757,487 | A | * | 5/1998 | Kersey ............ 356/478 |
| 6,072,567 | A | | 6/2000 | Sapack |
| 6,097,487 | A | * | 8/2000 | Kringlebotn et al. ....... 356/450 |
| 6,601,671 | B1 | * | 8/2003 | Zhao et al. ............ 181/108 |
| 6,785,004 | B2 | * | 8/2004 | Kersey et al. ........... 356/478 |
| 7,060,967 | B2 | * | 6/2006 | Thingbo et al. ......... 250/227.18 |
| 7,157,693 | B2 | * | 1/2007 | Thingbo et al. ......... 250/227.18 |
| 7,282,698 | B2 | | 10/2007 | Childers |
| 7,781,724 | B2 | * | 8/2010 | Childers et al. ........ 250/227.14 |
| 8,009,946 | B2 | * | 8/2011 | Xia et al. ............ 385/37 |
| 2003/0127232 | A1 | | 7/2003 | Bussear et al. |
| 2007/0065077 | A1 | * | 3/2007 | Childers et al. ........... 385/37 |
| 2008/0030729 | A1 | | 2/2008 | DiFoggio |
| 2008/0309945 | A1 | * | 12/2008 | Kojima et al. ............ 356/478 |
| 2011/0097031 | A1 | * | 4/2011 | Carralero et al. ........... 385/12 |
| 2011/0110620 | A1 | * | 5/2011 | Childers et al. ........... 385/13 |

OTHER PUBLICATIONS

Froggatt, M., Moore, J., "Distributed measurement of static strain in an optical fiber with multiple Bragg gratings at nominally equal wavelengths", Applied Optics 37 (10), Apr. 1, 1998.
Notification of Transmittal of the International Search Report and the Written Opinion of the International Searching Authority, or the Declaration; PCT/US2010/056204; Jul. 20, 2011.

* cited by examiner

Primary Examiner — Akm Enayet Ullah
(74) *Attorney, Agent, or Firm* — Cantor Colburn LLP

(57) ABSTRACT

An apparatus for estimating a parameter at distributed locations, the apparatus including: an optical fiber having: a first series of fiber Bragg gratings (FBGs) and configured to measure the parameter at a portion of the distributed locations; a second series of FBGs and configured to measure the parameter at another portion of the distributed locations; and an optical interrogator configured to illuminate the optical fiber and to receive light signals resulting from the illumination, the light signals including first light signals from the first series of FBGs within a first range of wavelengths, second light signals from the second series of FBGs within a second range of wavelengths, and other light signals within a third range of wavelengths, the ranges of wavelengths being distinct from each other; wherein the first light signals and the second light signals are used to estimate the parameter at the distributed locations.

21 Claims, 6 Drawing Sheets

$\lambda_A$ range includes first nominal reflection wavelength
$\lambda_B$ range includes second nominal reflection wavelength

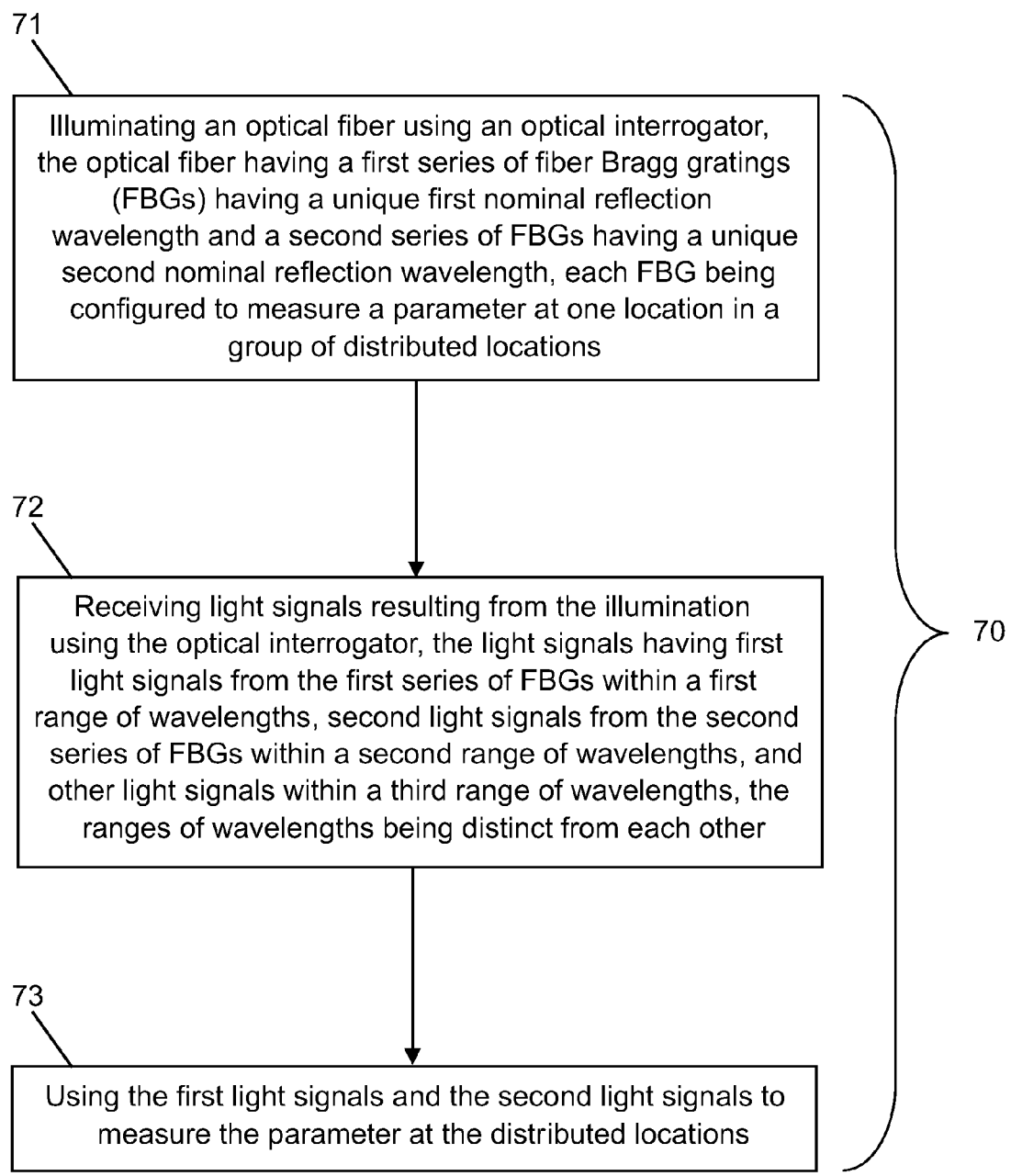

SENSOR ARRAY CONFIGURATION FOR EXTENDING USEFUL SENSING LENGTH OF A SWEPT-WAVELENGTH INTERFEROMETRY BASED SYSTEM

BACKGROUND OF THE INVENTION

1. Field of the Invention

The present invention relates to performing distributed measurements in a borehole penetrating the earth. More particularly, the measurements are performed using an optical reflectometer.

2. Description of the Related Art

In exploration and production of hydrocarbons, it is often necessary to drill a borehole into the earth to gain access to the hydrocarbons. Equipment and structures, such as borehole casings for example, are generally disposed into a borehole as part of the exploration and production. Unfortunately, the environment presented deep into the borehole can place extreme demands upon the equipment and structures disposed therein. For example, the equipment and structures can be exposed to high temperatures and pressures that can effect their operation and longevity.

In order to monitor the health of the equipment and structures disposed downhole, a fiber-optic distributed sensing system (DSS) may be used. Sensing fiber (an optical fiber containing sensors or in itself functioning as a sensor or sensors may be attached to the equipment and structures at various locations usually at different depths in the borehole. The sensors can measure temperature, pressure, strain, and other parameters. By measuring strain for example, the system can determine if borehole casing is being deformed.

In one type of DSS optical frequency domain reflectometry or swept-wavelength interferometry can be used to interrogate a series of fiber Bragg gratings. Each fiber Bragg grating (FBG) in the series acts as a sensor. The optical fiber, in one example, is affixed to casing wrapped along a length of the casing. As each FBG is exposed to a changing condition, the optical characteristics of each FBG will change in relation to the changed condition. A sensor interrogator is used to measure the optical characteristics of each of the FBGs in order to ascertain the changing conditions.

FIG. 1 presents an example of a conventional Optical Frequency Domain Reflectometry (OFDR) system. In this example, the optical fiber includes a reference reflector and a series of FBGs. A swept-wavelength light source is coupled to the fiber. The wavelength of light from the light source is swept to interrogate each of the FBGs. The reference reflector forms an interferometric cavity, such as a Fabry-Perot cavity in this example, with each individual FBG.

As the wavelength of light from the light source is swept, an interferogram is created with a frequency for each interferometric cavity that is proportional to the length of the cavity for each FBG. Thus, spectral data from each FBG is modulated with a unique frequency, which ultimately permits individual inspection of the FBGs through conventional signal processing techniques. Converting the spectral data into the spatial frequency domain through a Fast Fourier Transform yields a view of the fiber that is the amplitude of the reflected light as a function of distance. In this manner, each FBG can be monitored and treated as an individual sensor.

In the conventional sensing fiber depicted in FIG. 1, the fiber is configured in such a way that the length of "blank fiber" (i.e., optical fiber with no FBGs) is approximately the same as the length of fiber with FBGs. This blank fiber is located between the reference reflector and the FBGs to ensure that autocorrelation terms, i.e., those reflections resulting from FBGs interfering with other FBGs in the fiber, are located in the lower band of the spatial frequency domain. Thus, undesirable autocorrelation terms are separated from desirable FBG profiles, thereby, removing the corrupting effects.

Unfortunately, with the conventional OFDR system, only "X" distance of the sensing fiber can provide for sensing as depicted in FIG. 1. Sensing lengths of the fiber cannot be made arbitrarily long because of constraints resulting from the necessity to digitize the data coming back from the sensing fiber. For example, as the effective optical distance between a FBG and a reference reflector increases, the frequency of the modulation from that FBG also increases. Thus, a practical limit on the sensing length is the speed at which the signals from the FBGs can be sampled. Additionally, it is typically true that the longer the sensing length, the more susceptible the FBG signals are to corruption from vibration of the sensing fiber.

Therefore, what are needed are techniques to increase the sensing length of an optical fiber for OFDR. Preferably, the sensing length is increased without incurring penalties due to higher sampling requirements or increased susceptibility to vibration.

BRIEF SUMMARY OF THE INVENTION

Disclosed is a an apparatus for estimating a parameter at distributed locations, the apparatus including: an optical fiber having: a first series of fiber Bragg gratings (FBGs) configured to measure the parameter at a portion of the distributed locations, each FBG in the first series having a first nominal reflection wavelength; a second series of FBGs configured to measure the parameter at another portion of the distributed locations, each FBG in the second series having a second nominal wavelength; and an optical interrogator configured to illuminate the optical fiber and to receive light signals resulting from the illumination, the light signals including first light signals from the first series of FBGs within a first range of wavelengths, second light signals from the second series of FBGs within a second range of wavelengths, and other light signals within a third range of wavelengths, the ranges of wavelengths being distinct from each other; wherein the first light signals and the second light signals are used to estimate the parameter at the distributed locations.

Also disclosed is a method for estimating a parameter at distributed locations, the method including: illuminating an optical fiber disposed at the distributed locations using an optical interrogator, the optical fiber having: a first series of fiber Bragg gratings (FBGs) configured to measure the parameter at a portion of the distributed locations, each FBG in the first series having a first nominal reflection wavelength; a second series of FBGs configured to measure the parameter at another portion of the distributed locations, each FBG in the second series having a second nominal wavelength; and receiving light signals resulting from the illumination using the optical interrogator, the light signals having first light signals from the first series of FBGs within a first range of wavelengths, second light signals from the second series of FBGs within a second range of wavelengths, and other light signals within a third range of wavelengths, the ranges of wavelengths being distinct from each other; wherein the first light signals and the second light signals are used to estimate the parameter at the distributed locations.

Further disclosed is a non-transitory computer-readable medium comprising computer-executable instructions for estimating a parameter at distributed locations by implementing a method including: illuminating an optical fiber disposed at the distributed locations using an optical interrogator, the optical fiber having: a first series of fiber Bragg gratings (FBGs) configured to measure the parameter at a portion of the distributed locations, each FBG in the first series having a first nominal reflection wavelength; a second series of FBGs configured to measure the parameter at another portion of the distributed locations, each FBG in the second series having a second nominal wavelength; and receiving light signals resulting from the illumination using the optical interrogator, the light signals comprising first light signals from the first series of FBGs within a first range of wavelengths, second light signals from the second series of FBGs within a second range of wavelengths, and other light signals within a third range of wavelengths, the ranges of wavelengths being distinct from each other; wherein the first light signals and the second light signals are used to estimate the parameter at the distributed locations.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

FIG. 7 depicts an exemplary method for measuring a parameter at distributed locations.

DETAILED DESCRIPTION OF THE INVENTION

Disclosed are techniques for increasing a sensing length of an optical fiber used in an optical frequency domain reflectometry OFDR) sensing system. The techniques do not incur penalties due to higher sampling requirements or increased susceptibility to vibration of the optical fiber, and do not require additional downhole hardware to manage the "blank" fiber that would normally be required. The techniques, which include apparatus and method, call for making efficient use of available wavelengths of light signals. Measurements are obtained from at least two sets of fiber Bragg gratings (FBGs) using light signals. The light signals from each set have a distinct range of wavelengths, which generally do not overlap. Autocorrelation terms, redundant measurement terms, or other undesirable light signals are relegated by design to substantially the same range of wavelengths. Hence, because undesirable light signals are confined to the same range of wavelengths, more wavelengths are available to provide useful measurements.

In one embodiment the techniques provide an optical sensing fiber having two sets of FBGs situated within two reference reflectors, each set of FBGs having a unique nominal frequency of reflection. The techniques call for interrogating each FBG in one set by creating an optical cavity between each FBG in the one set and the reference reflector that is furthest away from the set. Because each optical cavity is formed with the furthest away reference reflector, the undesirable autocorrelation terms associated with each set are in the lower band of the spatial frequency domain and, thus, can be identified and filtered out. Thus, the techniques make use of the blank fiber length in the conventional OFDR sensing systems.

Before the techniques are discussed in detail, certain definitions are presented. The term "fiber Bragg grating" (FBG) relates to an optical fiber having a periodic variation to the refractive index of the fiber core resulting in a wavelength specific dielectric mirror. The FBG acts as a wavelength-specific reflector having a reflection frequency or wavelength. As the environment to which a FBG is exposed changes, the periodic variation to the refractive index changes causing a shift in the reflection wavelength. The shift may then be correlated to the change in the environment or environmental parameter. Non-limiting examples of the environmental parameter include temperature, pressure, force, strain, acceleration, and shape. Hence, the FBG can be a sensor for these parameters. The term "nominal refection wavelength" relates to the wavelength at which each FBG is designed to reflect light recognizing that manufacturing imperfections may cause the actual wavelength to vary slightly from the design wavelength.

Figure 2:
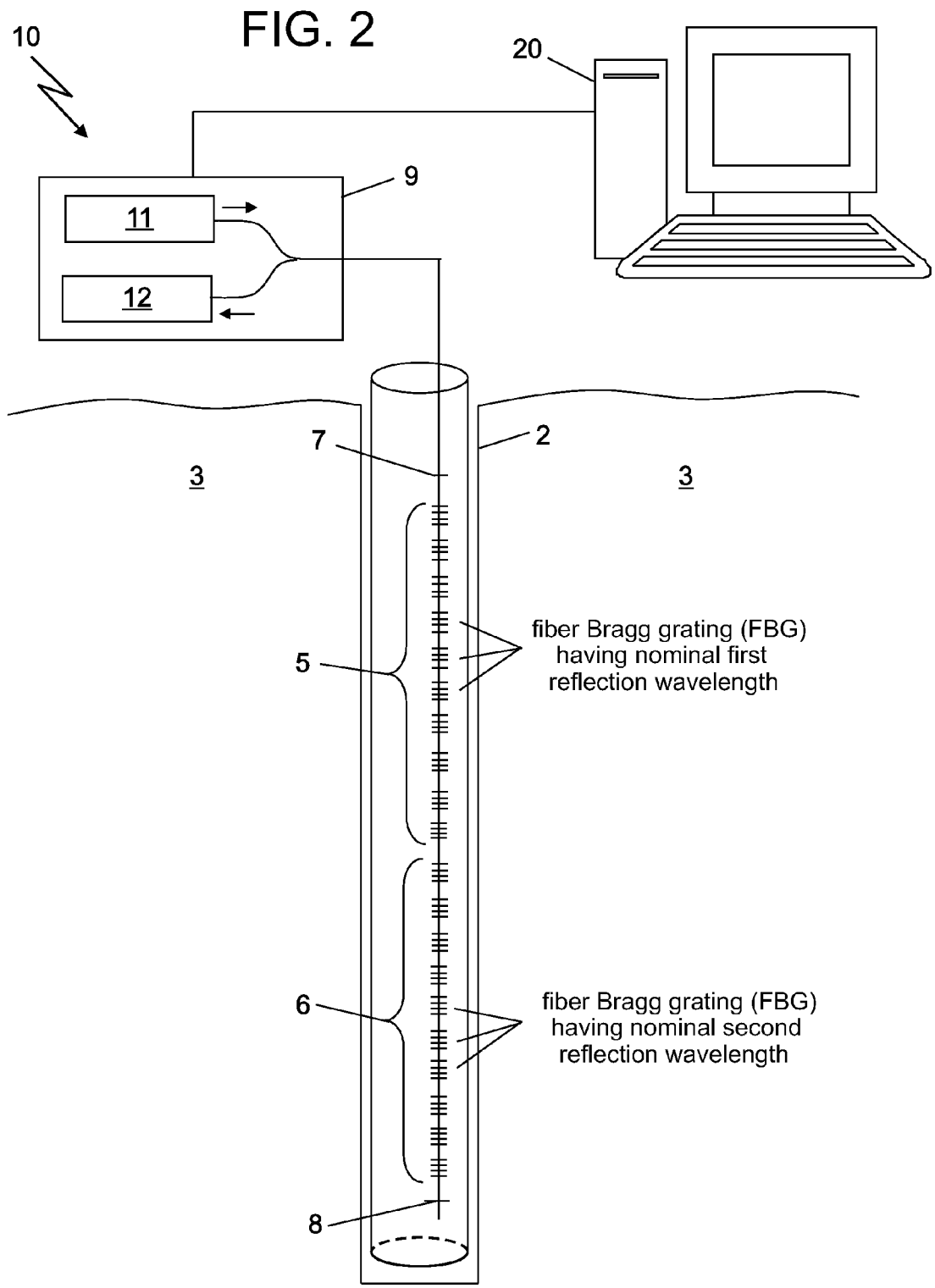
FIG. 2 illustrates an exemplary embodiment of a multi-reflector optical frequency domain reflectometry (OFDR) sensing system disposed at a casing in a borehole penetrating the earth.

Reference may now be had to FIG. 2. FIG. 2 illustrates an exemplary embodiment of a multi-reflector OFDR sensing system 10 coupled to a casing 21 lining a borehole 2 penetrating the earth 3. The casing 21 generally is used for hydrocarbon production purposes, but may represent any equipment or structure that may be monitored by the multi-reflector OFDR sensing system 10. The multi-reflector OFDR sensing system 10 includes an optical fiber 4 having a first set of FBGs 5 and a second set of FBGs 6 where each set is a series of FBGs. Each FBG in the first set of FBGs 5 has a first reflection wavelength $\lambda_1$ and each FBG in the second set of FBGs 6 have a second reflection wavelength $\lambda_2$. The first set of FBGs 5 and the second set of FBGs 6 are situated between a first reference reflector 7 and a second reference reflector 8. In the embodiment of FIG. 2, the first reference reflector 7 is configured to form an optical interferometric cavity, such as a Fabry-Perot cavity, with each FBG in the second set of FBGs 6. Similarly, the second reference reflector 8 is configured to form an optical cavity with each FBG in the first set of FBGs 5. In that the first reference reflector 7 must pass and reflect light, the first reference reflector 7 is a partial reflector.

Figure 1:
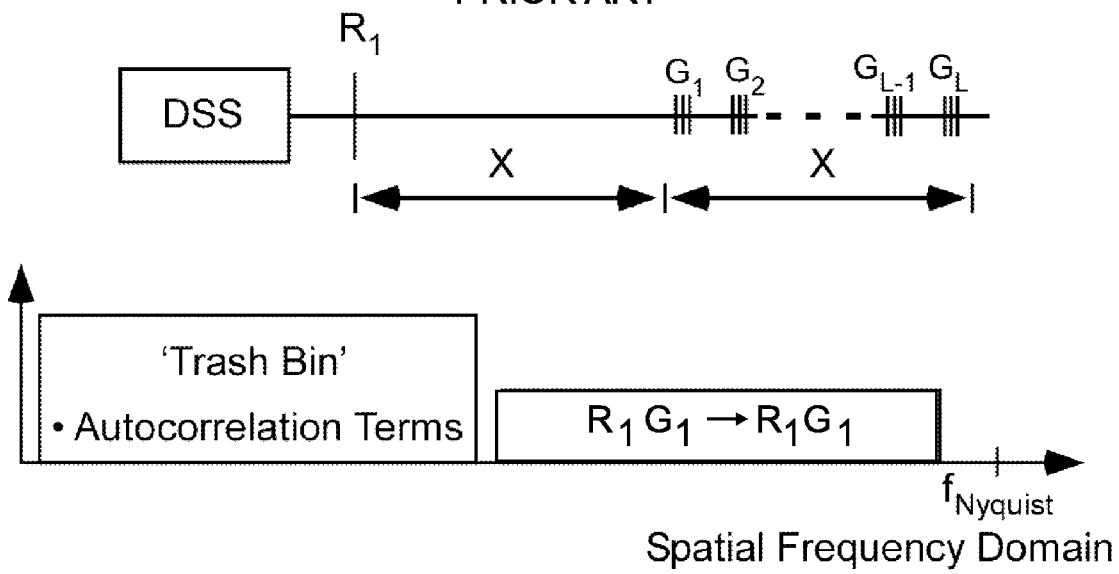
FIG. 1 illustrates a prior art optical frequency domain reflectometry sensing system.
Figure 3:
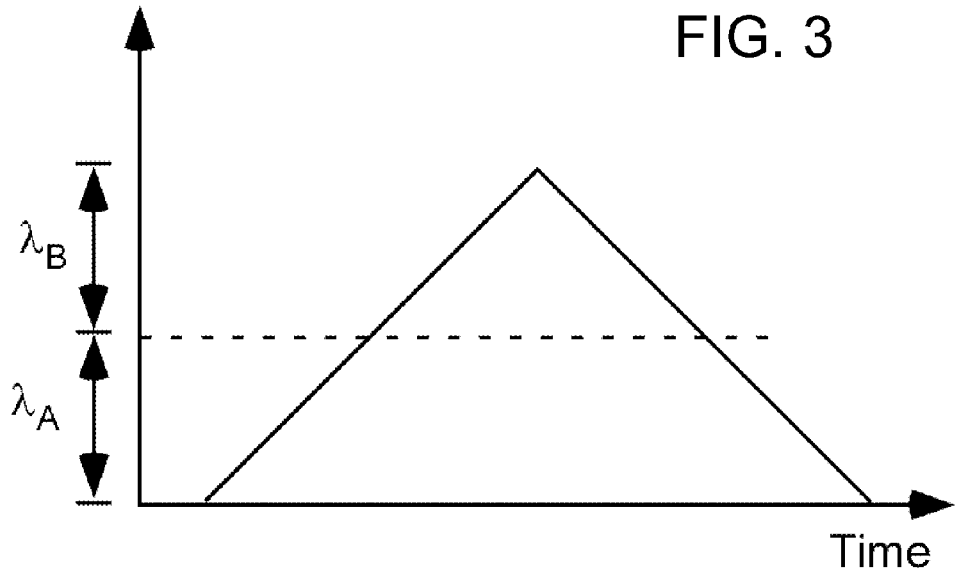
FIG. 3 depicts aspects light used for interrogating a sensing fiber in the OFDR sensing system.

Still referring to FIG. 2, the multi-reflector OFDR sensing system 10 includes an optical interrogator 9. The optical interrogator 9 is configured to obtain measurement data from each individual FBG in the optical fiber 4. To obtain the data, the optical interrogator 9 includes a light source 11 such as a tunable laser and a photodetector 12. The light source 11 is configured to illuminate the optical fiber 4 with wavelengths of light swept about each of the first reflection wavelength $\lambda_1$ and the second reflection wavelength $\lambda_2$. FIG. 3 provides one example of a swept pattern of wavelengths of light provided by the light source 11 to the optical fiber 4. The swept pattern of wavelengths includes two ranges ($\lambda_A$) and ($\lambda_B$). It is necessary that each wavelength range encompass a sufficient range to meet the dynamic sensing range for the application.

The swept wavelengths of light illuminating the optical fiber 4 create an interferogram from the various interferences of light from the various optical interferometric cavities. The interferogram is a record of the light interferences with each light interference having a reflection wavelength and a magnitude of the reflected light. The photodetector 12 is configured to receive and measure the light reflected from the optical fiber 4 at the various wavelengths and associated magnitudes in order to create the interferogram. The interferogram may be created by the optical interrogator 9 or by a computer processing system 20 coupled to the interrogator 9.

From the interferogram, measurement data from each FBG in the optical fiber 4 may be obtained. In general, an interference is associated with each of the FBGs. The wavelength of the interference identifies the individual FBG and the magnitude of the reflected light at the wavelength is the measurement data.

Figure 4:
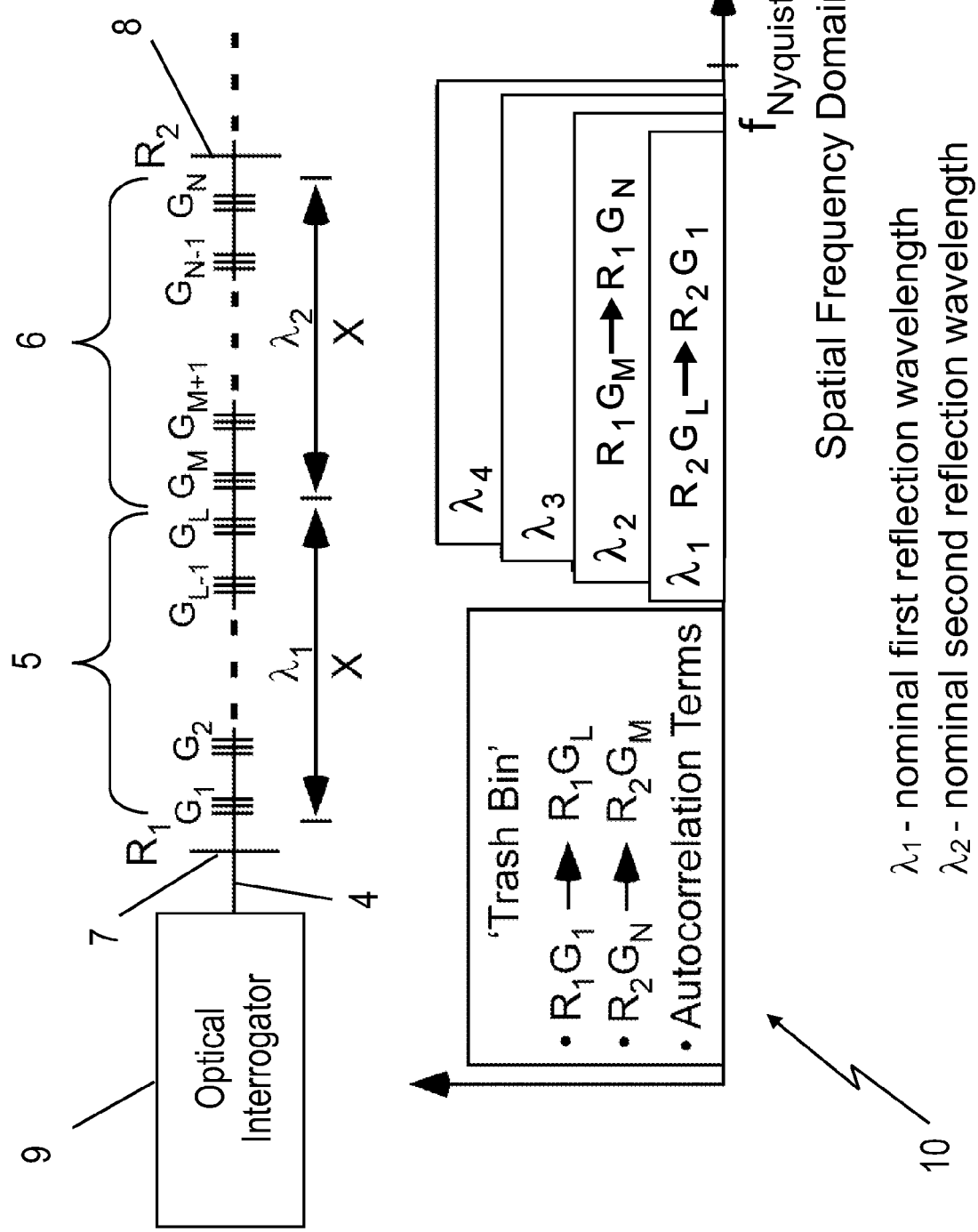
FIG. 4 depicts aspects of the multi-reflector OFDR sensing system having two sets of fiber Bragg gratings (FBGs) situated between two reference reflectors.

Reference may now be had to FIG. 4. FIG. 4 depicts aspects of obtaining the measurement data from the individual FBGs. In the embodiment of FIG. 4, the length (X) of the portion of the optical fiber 4 having the first set of FBGs 5 is substantially the same as the length (X) of the portion having the second set of FBGs 6. The optical interrogator 9 illuminates the optical fiber 4 and processes the resulting interference patterns.

As part of the processing, the interferences resulting from optical cavities formed by the first reference reflector 7 and the second set of FBGs 6 and from optical cavities formed by the second reference reflector 8 and the first set of FBGs 5 are used to identify the individual FBGs and their associated measurement data. Autocorrelation terms and data from interferences resulting from optical cavities formed by the first reference reflector 7 and the first set of FBGs 5 and optical cavities formed by the second reference reflector 8 and the second set of FBGs 6 are, by design, relegated to a similar range of frequencies that are not useful and, thus, filtered out (i.e., placed in 'trash bin'). That is, autocorrelation terms, which are not useful, have a certain range of frequencies that is different from the range of frequencies of the light interferences that provide useful sensing measurements from all the FBGs. Because the light interferences providing useful sensing measurements are in a separate range of frequencies, any other light interferences do not provide anymore useful measurements and are thus designed to be relegated into substantially the same range of frequencies as the autocorrelation terms.

In one embodiment, when all of the interferences are received, the interferences are transformed into a spatial frequency domain using a Fast Fourier Transform. In the spatial frequency domain, each FBG is associated with a frequency or range of frequencies that is/are used to locate that FBG along the optical fiber 4 (i.e., at a space within the optical fiber 4). In general, as the distance from a reference reflector to an FBG increases, the frequency identifying that FBG also increases. Thus, the discarded data is identified as being in the lower band of the spatial frequency domain.

Figure 5:
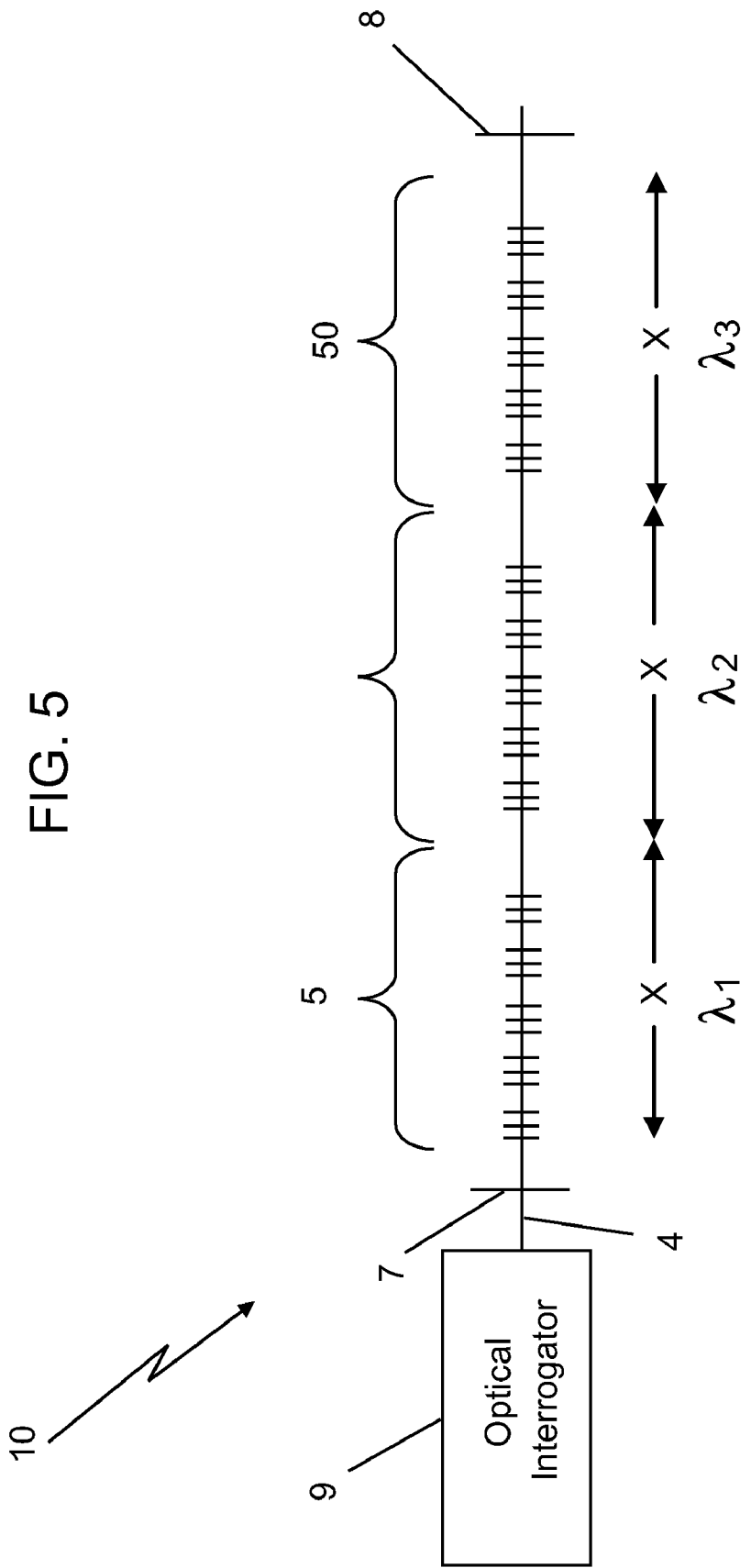
FIG. 5 depicts aspects of the multi-reflector OFDR sensing system having three sets of FBGs situated between two reference reflectors.
Figure 6:
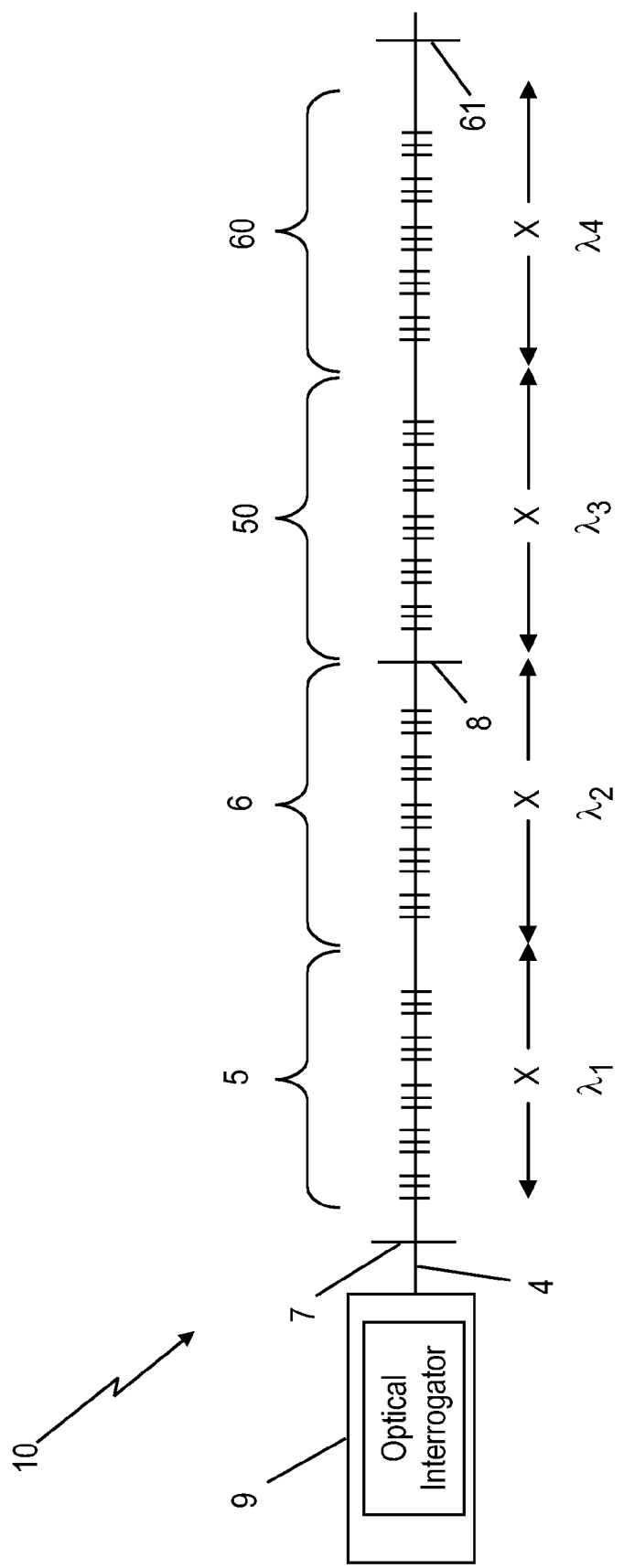
FIG. 6 depicts aspects of the multi-reflector OFDR sensing system having three reference reflectors.

While the embodiments presented above disclose using two separate sets of FBGs where each set has a unique reflection wavelength, the techniques are applicable to embodiments having three or more sets of FBGs with each set having a unique reflection wavelength. In embodiments having three or more sets of FBGs disposed between two reference reflectors, the measurement data is generally obtained from interferences resulting from optical cavities formed between each set of FBGs and the reference reflector that is furthest away from the set of interest. FIG. 5 illustrates an exemplary embodiment of a third set of FBGs 50 disposed between the first reference reflector 7 and the second reference reflector 8. In the embodiment of FIG. 5, measurements performed by the third set of FBGs 50 are polled by the optical interrogator 9 using interferences of light from optical cavities formed by the first reference reflector 7 and the third set of FBGs. In another embodiment, the third set of FBGs 50 and a fourth set of FBGs 60 are disposed between the second reference reflector 8 and a third reference reflector 61 as shown in FIG. 6. The second reference reflector 8 in the embodiment of FIG. 6 is a partial reflector. Measurements performed by the third set of FBGs 50 and the fourth set of FBGs 60 are polled using optical cavities formed by the second reference reflector 8 and each FBG in the fourth set of FBGs 60 and by the third reference reflector 61 and each FBG in the third set of FBGs 50.

The technique of adding additional sets of FBGs to the optical fiber 4 may be repeated a number of times with each additional set of FBGs yielding an additional length X (with reference to FIG. 4) of effective sensing length. The natural limit to adding additional sets of FBGs is dictated by the wavelength range of the light source 11 used in the optical interrogator 9 and the dynamic range required for a sensing application. For example, in steam assisted gravity drainage (SAGD) applications it is desired to monitor temperature along wells. Because the dynamic sensing range is small for the expected temperatures, the dynamic wavelength range is also small, thus, allowing many sets of FBGs with differing reflection wavelengths. Hence, for this type of application, the optical fiber 4 can be tens of kilometers long, which is much longer than conventional OFDR sensing systems.

FIG. 7 presents one example of a method 70 for measuring a parameter at distributed locations. The method 70 calls for (step 71) illuminating the optical fiber 4 using the optical interrogator 9. Further, the method 70 calls for (step 72) receiving light signals resulting from the illumination using the optical interrogator 9 wherein the light signals include first light signals from the first series of FBGs within a first range of wavelengths, second light signals from the second series of FBGs within a second range of wavelengths, and other light signals within a third range of wavelengths, the ranges of wavelengths being distinct from each other. Further, the method 70 calls for (step 73) using the first light signals and the second light signals to measure the parameter at the distributed locations.

In support of the teachings herein, various analysis components may be used, including a digital and/or an analog system. For example, the optical interrogator 9 or the computer processing system 20 may include the digital and/or analog system. The system may have components such as a processor, storage media, memory, input, output, communications link (wired, wireless, pulsed mud, optical or other), user interfaces (e.g., display or printer), software programs, signal processors (digital or analog) and other such components (such as resistors, capacitors, inductors and others) to provide for operation and analysis of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical coupler, optical splitter, optical unit, electrical unit or electromechanical unit may be included in support of the various aspects discussed herein or in support of other functions beyond this disclosure.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first," "second," "third," "fourth," and "fifth" are used to distinguish elements and are not used to denote a particular order. The term "couple" relates to coupling one component to another component either directly or indirectly via an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating a parameter at distributed locations, the apparatus comprising:
    an optical fiber comprising:
        a first series of fiber Bragg gratings (FBGs) configured to measure the parameter at a portion of the distributed locations, each FBG in the first series having a first nominal reflection wavelength;
        a second series of FBGs configured to measure the parameter at another portion of the distributed locations, each FBG in the second series having a second nominal wavelength; and
    an optical interrogator configured to illuminate the optical fiber and to receive light signals resulting from the illumination, the light signals comprising first light signals from the first series of FBGs within a first range of wavelengths, second light signals from the second series of FBGs within a second range of wavelengths, and other light signals within a third range of wavelengths, the ranges of wavelengths being distinct from each other;
    wherein the first light signals and the second light signals are used to estimate the parameter at the distributed locations.

2. The apparatus of claim 1, wherein the other light signals comprise autocorrelation terms, redundant information from the first series, redundant information from the second series, or combination thereof.

3. The apparatus of claim 2, further comprising:
    a first reference reflector disposed at the optical fiber; and
    a second reference reflector disposed at the optical fiber;
    wherein the first series of FBGs and the second series of FBGs are situated between the first reference reflector and the second reference reflector with the first series of FBGs being optically closest to the first reference reflector; the first light signals comprising light interferences resulting from optical cavities formed by the first reference reflector and each of the FBGs in the second series; and the second light signals comprising light interferences resulting from optical cavities formed by the second reference reflector and each of the FBGs in the first series.

4. The apparatus of claim 3, wherein the optical interrogator is further configured to illuminate the optical cavities with light by sweeping through the first range of wavelengths and the second range of wavelengths.

5. The apparatus of claim 3, wherein at least one of the first reference reflector and the second reference reflector are partial reflectors configured to pass light and reflect light.

6. The apparatus of claim 3, wherein the third range of wavelengths comprises wavelengths that are greater than the wavelengths in the first range of wavelengths and the second range of wavelengths.

7. The apparatus of claim 3, the optical fiber further comprising a third series of FBGs disposed between the first reference reflector and the second reference reflector, each FBG in the third series having a third nominal reflection wavelength, wherein third light signals within a fourth range of wavelengths include light interferences from optical cavities formed by each FBG in the third series and one of the first reference reflector and the second reference reflector are used to measure the parameter at the distributed locations associated with the FBGs in the third series.

8. The apparatus of claim 3, the optical fiber further comprising:
    a third reference reflector;
    a third series of FBGs situated between the second reference reflector and the third reference reflector, each FBG in the third series having a third nominal reflection wavelength, the third series being configured to provide third light signals within a fourth range of wavelengths that includes light interferences from optical cavities formed by each FBG in the third series and the third reference reflector;
    a fourth series of FBGs situated between the second reference reflector and the third reference with the third series being optically closest to the second reference reflector, each FBG in the fourth series having a fourth nominal reflection wavelength, the fourth series being configured to provide fourth light signals within a fifth range of wavelengths that includes light interferences from optical cavities formed by each FBG in the fourth series and the second reference reflector;
    wherein the third light signals are used to measure the parameter at the distributed locations associated with the FBGs in the third series and the fourth light signals are used to measure the parameter at the distributed locations associated with the FBGs the fourth series.

9. The apparatus of claim 1, wherein the optical interrogator is configured to transform the light signals with a Fast Fourier Transform into a spatial frequency domain.

10. The apparatus of claim 9, wherein the light signals in the spatial frequency domain comprise a frequency or range of frequencies related to a location of a specific FBG in one of the first series and the second series and an amplitude at the frequency or range of frequencies related to a magnitude of the parameter being measured by the specific FBG.

11. The apparatus of claim 1, wherein a length of the portion of distributed locations at the optical fiber is substantially equal to the length of the another portion of distributed locations.

12. The apparatus of claim 1, wherein the parameter comprises at least one of temperature, pressure, force, strain, acceleration, and shape.

13. The apparatus of claim 1, wherein the optical fiber is coupled to a component disposed in a borehole penetrating the earth.

14. The apparatus of claim 11, wherein the component is a borehole casing.

15. A method for estimating a parameter at distributed locations, the method comprising:
   illuminating an optical fiber disposed at the distributed locations using an optical interrogator, the optical fiber comprising:
      a first series of fiber Bragg gratings (FBGs) configured to measure the parameter at a portion of the distributed locations, each FBG in the first series having a first nominal reflection wavelength;
      a second series of FBGs configured to measure the parameter at another portion of the distributed locations, each FBG in the second series having a second nominal wavelength; and
   receiving light signals resulting from the illumination using the optical interrogator, the light signals comprising first light signals from the first series of FBGs within a first range of wavelengths, second light signals from the second series of FBGs within a second range of wavelengths, and other light signals within a third range of wavelengths, the ranges of wavelengths being distinct from each other;
   wherein the first light signals and the second light signals are used to estimate the parameter at the distributed locations.

16. The method of claim 15, wherein illuminating comprises sweeping through the first range of wavelengths and the second range of wavelengths.

17. The method of claim 15, further comprising transforming the light signals with a Fast Fourier Transform into a spatial frequency domain.

18. The method of claim 17, wherein the light signals in the spatial frequency domain comprise a frequency or range of frequencies related to a location of a specific FBG in one of the first series and the second series and an amplitude at the frequency or range of frequencies related to a magnitude of the parameter being measured by the specific FBG.

19. The method of claim 15, further comprising:
   illuminating in the optical fiber a third series of FBGs situated between the first reference reflector and the second reference reflector using the optical interrogator, each FBG in third series having a third nominal reflection wavelength; and
   receiving third light signals within a fourth range of wavelengths resulting from the illumination of the third series using the optical interrogator, the third light signals comprising light interferences from optical cavities formed by each FBG in the third series and one of the first reflector and the second reflector;
   wherein the third light signals are used to measure the parameter at the distributed locations associated with the FBGs in the third series.

20. The method of claim 15, further comprising:
   illuminating in the optical fiber a third series of FBGs and a fourth series of FBGs being situated between the second reference reflector and a third reference reflector with the third series being optically closest to the second reference reflector, each FBG in the third series having a third nominal reflection frequency, each FBG is the fourth series having a fourth nominal reflection frequency;
   receiving third light signals within a fourth range of wavelengths resulting from the illumination of the third series, the third light signals having light interferences from optical cavities formed by each FBG in the third series and the third reference reflector;
   receiving fourth light signals within a fifth range of wavelengths resulting from the illumination of the fourth series, the fourth light signals having light interferences resulting from optical cavities formed by each FBG in the fourth series and the second reference reflector;
   wherein the third light signals are used to measure the parameter at the distributed locations associated with the FBGs in the third series and the fourth light signals are used to measure the parameter at the distributed locations associated with the FBGs the fourth series.

21. A non-transitory computer-readable medium comprising computer-executable instructions for estimating a parameter at distributed locations by implementing a method comprising:
   illuminating an optical fiber disposed at the distributed locations using an optical interrogator, the optical fiber comprising:
      a first series of fiber Bragg gratings (FBGs) configured to measure the parameter at a portion of the distributed locations, each FBG in the first series having a first nominal reflection wavelength;
      a second series of FBGs configured to measure the parameter at another portion of the distributed locations, each FBG in the second series having a second nominal wavelength; and
   receiving light signals resulting from the illumination using the optical interrogator, the light signals comprising first light signals from the first series of FBGs within a first range of wavelengths, second light signals from the second series of FBGs within a second range of wavelengths, and other light signals within a third range of wavelengths, the ranges of wavelengths being distinct from each other;
   wherein the first light signals and the second light signals are used to estimate the parameter at the distributed locations.

* * * * *